_United States Patent_ [19]

Allen

[11] 4,255,590

[45] Mar. 10, 1981

[54] COMBINATION OF PYROLYSIS AND INCINERATION OF SOLID MIXTURE OF OXYGEN-CONTAINING AROMATIC COMPOUNDS OBTAINED AS RESIDUE OF MANUFACTURE OF BENZENE DI- AND TRICARBOXYLIC ACIDS

[75] Inventor: John K. Allen, St. Charles, Ill.

[73] Assignee: Standard Oil Company (Indiana), Chicago, Ill.

[21] Appl. No.: 92,570

[22] Filed: Nov. 8, 1979

[51] Int. Cl.$^3$ .............................................. C07C 51/16
[52] U.S. Cl. ................................................... 562/416
[58] Field of Search ........................................ 562/416

[56] References Cited

U.S. PATENT DOCUMENTS 3,880,920   4/1975   Wampfler ............................ 562/416

_Primary Examiner_—Paul J. Killos

_Attorney, Agent, or Firm_—Fred R. Ahlers; William T. McClain; William H. Magidson

[57] ABSTRACT

Solid residues obtained from the manufacture of benzene di- or tricarboxylic acid by the oxidation of di- or trimethyl substituted benzene with air in the presence of catalysis from a source of bromine in combination with one or both of cobalt and manganese when incinerated can produce bromine-containing particulates whose discharge into the atmosphere may be undesirable. The discharge of such bromine-containing particles into the atmosphere can be avoided by subjecting said solid residue in comminuted form or such form suspended in 30 to 50 weight percent water to continuous pyrolysis in the presence of an inert particulate solid in a zone heated to a temperature of at least 700° C., contacting the gaseous product or a portion thereof after removal of benzene and toluene therefrom with a carbonate, hydroxide or oxide of one or both of calcium and magnesium and then incinerating the gaseous product or said portion thereof.

3 Claims, No Drawings

COMBINATION OF PYROLYSIS AND INCINERATION OF SOLID MIXTURE OF OXYGEN-CONTAINING AROMATIC COMPOUNDS OBTAINED AS RESIDUE OF MANUFACTURE OF BENZENE DI- AND TRICARBOXYLIC ACIDS

FIELD OF INVENTION

This invention relates to the disposal of oxygen-containing aromatic compounds obtained as a residual solid mixture from the manufacture of aromatic acids. More specifically the present invention relates to said disposal of such solid residue by non-catalytic pyrolysis at a temperature of at least 700° C. and burning at least the gaseous product and the char if any is formed by the pyrolysis.

STATE OF THE ART

The thermal stability of benzoic acid, and o-phthalic acid was investigated in the early 1930s in the absence and in the presence of decarboxylation catalysts. While the decarboxylation of o-phthalic acid to benzoic acid and trimellitic acid to o-phthalic acid were the stated purposes of those specific thermal reactions, the decarboxylation of benzoic acid to benzene appeared to be of academic interest. The following provides a more complete but not exhaustive insight into the thermal decarboxylation and decarbonylation of aldehydo- or carboxy-substituted benzenes.

The thermal decomposition of benzoic acid to benzene and carbon dioxide begins non-catalytically at 370° C. in a glass bulb and is substantially complete at 400° C. (Chemical Abstracts, vol. 41, 646) according to the original article of Wolfgang Mosher in Helv. Chem. Acta. 14, 917–97 (1931) and such dissociation is accelerated by copper and calcium catalysts. Said dissociation occurs at temperatures as low as 245° to 250° C. in the presence of Zn—Cu—Cr oxide-type catalysts according to Corliss R. Kinney and David P. Langlois in J. Am. Chem. Soc., vol. 53, 2189–2192 (1931). Decarbonylation of benzaldehyde to high yields of benzene is aided by plasma of glow discharge according to Published Patent Application ("Offenlegungschrift") No. 2,038,272 of the Federal German Republic published Mar. 16, 1972. According to British Pat. No. 735, 300 published Aug. 17, 1955 toluic acids heated to 400° C. in the presence of chromites of Zn, Cd, Zn—Cd, Zn—Fe or ZnO with either CuO or CdO are converted to toluene.

The preparation of benzoic acid by the thermal decarboxylation of phthalic acids in the presence of steam is known to be generally conducted in the presence of a catalyst such as nickel phthalate at 175° to 350° C. according to U.S. Pat. No. 1,962,175; 1 to 2% ammonia in the steam according to British Pat. No. 469,541 published July 29, 1932; $V_2O_5$ or ZnO on $Al_2O_3$ or $Al_2O_3$ alone according to Chemical Abstracts vol. 37, Col. 5383; carbon catalyst impregnated with hydroxides of both alkali and alkaline earth metals to effect the decarboxylation at temperatures at and below 400° C. according to U.S. Pat. No. 2,470,688; cobalt carbonyl, $Co_2(CO)_8$ used in an atmosphere of carbon monoxide and hydrogen converts phthalic acids and substituted phthalic acids to benzoic acid and substituted benzoic acid or cobalt carbonyl modified by trialkylphosphine ligands converts benzene polycarboxylic acids having COOH groups on adjacent ring carbon atoms to isoand terephthalic acids according to Chemical Abstracts, vol 81, entry 52064r. Also heating trimellitic acid to temperatures of 300° to 375° C. converts the tricarboxylic acid to o-phthalic acid according to U.S. Pat. No. 3,862,145.

From the state of the art at the time of making the present invention it appears that the main interest in decarboxylation of benzene carboxylic acids was to prepare a higher quality benzene carboxylic acid of lesser COOH group content from a benzene carboxylic acid of higher COOH group content and lower quality such as a coal acid or to obtain a benzene carboxylic acid of exceptionally high quality; e.g., pharmaceutical quality benzoic acid, from phthalic anhydride by converting it to o-phthalic acid and decarboxylating it. But there was no apparent interest in the decarboxylation of benzene carboxylic acids to aromatic hydrocarbons.

In an altogether different environment a new problem has arisen. In the commercial manufacture of benzene di- or tricarboxylic acids (e.g., isophthalic acid, terephthalic acid or trimellitic acid) there is obtained, after maximizing recovery of such acid and recovery for reuse the reaction solvent, a residue which is a mixture of oxygen-containing derivatives of benzene and toluene which are mono-, di- and tricarboxylic acids, aldehydo-carboxylic acids, and methylol-substituted benzene or toluene or their carboxylic (benzoic or toluic) acids and which also contains components of catalysis. Usually such components of catalysis are cobalt alone or in such combinations as Co—Mn—Br or Co—Mn—Ce—Br from liquid phase oxidation of a xylene or pseudocumene (1,2,4-trimethylbenzene) with air in the presence of acetic acid reaction solvent. A similar residue is also obtained from the neat oxidation of liquid o-xylene with air in the presence of Co—Mn—Br catalyst system after dehydrating the o-phthalic acid formed to its anhydride under conditions which vaporize the anhydride, water and materials boiling between the anhydride and water. While such residues amount to from 2 to 25 weight percent of the benzene di- or tricarboxylic acid produced, such residue production annually is substantial in view of the millions of kilograms of the benzene di- or tricarboxylic acids produced annually.

Such residues contain water-soluble benzene carboxylic acids and water-soluble forms of the components of catalysis. Landfill disposal of such residues is undesirable because rain and ground water leach out those carboxylic acids and soluble forms of the components of catalysis and can contaminate surface run off water and eventually streams as well as below surface aquafiers. Disposal of such residues can be made by incineration and use made of the resultant heat produced, but the metal catalyst components are converted to forms in the resultant ash which are difficult and/or expensive to convert to reusable forms for the oxidation of the methyl-substituted benzenes. Although in such residues the substituted benzene and toluene compounds whose substituents are the carboxy-, aldehydo- and methylol substituents are individually desirable and useful commercial products, it is not economically feasible to separate and recover the individual compounds from the residues.

When such residues contain bromides, bromine-containing particulates can be discharged into the atmosphere along with the combustion products of incineration. Such bromine contamination of the atmosphere may be or become undesirable.

We have in our laboratories investigated the use of suggested decarboxylation and/or decarbonylation catalyst with the study of thermal conversion of the before-described residues of the manufacture of benzene di- and tricarboxylic acid to useful chemical products. During such investigations we found that zinc oxide alone or with chromia, or molybdena or alumina were the most active of such previously suggested catalysts. But, as we also found, such zinc oxide-containing catalysts had a rather short activity life, above five days, when used with residue from the manufacture of terephthalic acid at a weight ratio of residue to catalyst of 2:1 and at a temperature of 500° C. Such short catalyst life would be commercially unattractive even for use in the disposal of residue from the manufacture of terephthalic acid.

However, we also discovered in our laboratories that the non-catalytic pyrolysis of the solid residues from the manufacture of a benzene di- or tricarboxylic acid could be effectively carried out by continuous operation at a temperature of at least 700° C. by two different techniques. One technique involves the continuous introduction of such solid residue in comminuted form per se or diluted by inert particles into a pyrolysis zone maintained at a temperature of at least 700° C. Under such conditions a gaseous product containing water vapor and vapors of benzene and toluene together with vapors of multi-ring (e.g., biphenyl, terphenyl and anthracene) aromatic compounds mixed with mainly the gases hydrogen, methane, oxides of carbon and lesser amounts of lower ($C_2$ to $C_4$) alkanes and alkenes; and a char containing 60% carbon and the components of the catalysis used in the manufacture of the benzene di- and tricarboxylic acids by catalytic liquid phase oxidation of di- and trimethyl benzenes with air. Such carbonaceous char per se or diluted with the inert particulates is discharged from the pyrolysis zone and can be extracted with acetic acid to remove 70 to 80 percent of the metal catalyst component (e.g., Co or Co and Mn) and 65 to 70 percent (both by weight) of the bromides, if bromine was used as a component of catalysis. The acetic acid insoluble portion of the carbonaceous product could then be incinerated as could be, of course, the carbonaceous product but with the penalty of making difficult the recovery of the metal catalysts from the resulting incineration ash. The catalyst metal components remain in the bed of particulates and can be extracted therefrom by acetic acid, hydrochloric or hydrobromic acid or sulfuric acid.

The second technique involves a pyrolysis zone maintained at a temperature of at least 700° C. and containing a bed of inert particulates whose particles are stimulated into motion as in a fluidized bed, expanded bed or a bed made ebullient by flow of gas through the bed of particulates to which is continuously fed a suspension in water (50 to 60 weight percent solids) of comminuted solid residue from benzene di- or tricarboxylic acid manufacture. By this technique the carbonaceous residue is not formed because it reacts with the water vapor according to the water-gas reaction to produce hydrogen and carbon dioxide which enrich their content in the before-described gaseous product.

Both continuous non-catalytic pyrolysis techniques described above produce gaseous products which can contain organic and inorganic bromides as does the carbonaceous char product of the first-described continuous pyrolysis technique when bromine and/or bromides are a component of the oxidation catalyst. But the incineration of the carbonaceous char or its acetic acid insoluble portions does not release bromine-containing particulates because the bromine or bromides are retained in the ash.

The process of this invention is directed at the prevention of escape into the atmosphere of bromine-containing particulates when the above gaseous product or its portion remaining after removal of benzene and toluene is burned to provide heat for the non-catalytic pyrolysis.

SUMMARY OF THE INVENTION

The present invention comprises the continuous non-catalytic pyrolysis at a temperature of at least 700° C., for example from 700° C. up to 900° C., of the solid residue obtained from the manufacture of a benzene di- or tricarboxylic acid using a catalyst system consisting essentially of a combination of bromine (per se or as an organic or inorganic bromide) with a metal oxidation catalyst which is cobalt or cobalt and manganese or cobalt, manganese and cerium to produce at least a gaseous product containing organic and inorganic bromides; vapors of water, benzene, toluene and multi-ring compounds and at least the gases hydrogen, oxides of carbon and methane; contacting such gaseous product with the oxide, hydroxide or carbonate of calcium or mixture of calcium and magnesium; and then incinerating the gaseous product or the portion thereof after the removal of benzene and toluene therefrom.

The present invention also includes incineration of the carbonaceous char or acetic acid insoluble portion thereof with the total gaseous product or its portion after removal of benzene and toluene thereof after the total gas has been contacted with the oxide, hydroxide or carbonate of calcium or mixture of calcium and magnesium.

The amount of oxide, hydroxide or carbonate of calcium or calcium and magnesium used in the present inventive process for disposing of the solid residue from benzene di- and tricarboxylic acid manufacture is at least one-half equivalent of the oxide, hydroxide or carbonate per equivalent of bromine present in such solid residue because about one-half of the bromine in such solid residue appears in the gaseous product. The practical amount of said oxide, hydroxide, or carbonate for adequate disposal of the solid residue is within the range from 0.5 up to 1.0 chemical equivalent per chemical equivalent of bromine present in such solid residue.

Residues from the manufacture of benzene di- and tricarboxylic acids in general contain from zero to five weight percent total of water and acetic acid, from three up to five weight percent total of components of catalyst and associated with the metals (usually in the plus two valence state) from three to ten weight percent acetate radical. Thus, the oxygen-containing aromatic compounds can comprise from 79 to 96 weight percent of the residue.

More specifically, the oxygen-containing aromatic compounds which can be present in the residues subjected to pyrolysis of this invention can be illustrated by the identified compounds present in the residue from the manufacture of terephthalic acid by the air oxidation of p-xylene in acetic acid as reaction solvent and in the presence of cobalt, manganese and bromine as components of the catalyst system. Such identified compounds are now known to be: terephthalic acid and its precursors p-toluic acid, p-formylbenzoic acid, p-tolualdehyde, terephthalaldehyde and p-methylbenzyl alcohol by-products including methylphthalic acids, ortho- and isophthalic acids (from o- and m-xylene impurities in the p-xylene), trimellitic acid, as well as benzaldehyde and benzoic acid (from ethylbenzene impurity in p-xylene); and co-products including 4,4'-bibenzoic acid; 1,2-bis (p-carboxyphenyl) ethane; 2,5,4'-tricarboxybiphenyl; 2,6-dicarboxyfluorenone; and 4,4'-stilbene dicarboxylic acid. On a water and acetic acid-free basis one such residue contains the weight percentages of the foregoing compounds and groups of compounds as shown in TABLE I to follow.

TABLE I

| COMPONENTS OF RESIDUE FREE OF WATER AND ACETIC ACID | |
|---|---|
| Terephthalic Acid | 26.4% |
| p-Toluic Acid | 20.8% |
| p-Formylbenzoic Acid | 9.1% |
| p-Tolualdehyde | 0.51% |
| Terephthalaldehyde | 1.20% |
| p-Methylbenzyl Alcohol | 2.06% |
| Reaction By-Products | 36.9% |
| Co-Products | 4.12% |

Another such residue has the composition including the catalyst components: cobalt, manganese and bromine and metals of corrosion as shown in TABLE II to follow.

TABLE II

| RESIDUE FROM TEREPHTHALIC ACID MANUFACTURE ON ACETIC ACID AND WATER-FREE BASIS | |
|---|---|
| Component | Weight Percent |
| Phthalic Acids | 19.0 |
| Benzoic Acid | 14.8 |
| Toluic Acids | 26.7 |
| Methyl Phthalic Acids | 2.65 |
| Trimellitic and Trimessic Acids | 4.32 |
| 4-Carboxybenzaldehyde | 9.09 |
| Tolualdehydes | 0.40 |
| Benzaldehyde | 0.004 |
| Terephthalaldehyde | 0.27 |
| Methylbenzyl Acetate | 0.02 |
| Formyl Acetate | 0.15 |
| Benzylbenzoate | 0.07 |
| Phthalide | 2.04 |
| Co-Products | 4.24 |
| Cobalt | 1.51 |
| Manganese | 2.53 |
| Bromine | 2.20 |
| Iron | 0.09 |
| Aluminum | 0.00022 |
| Calcium | 0.02 |
| Chromium | 0.007 |
| Copper | 0.0001 |
| Magnesium | 0.0028 |
| Molybdenum | 0.0035 |
| Sodium | 0.30 |
| Nickel | 0.0052 |
| Silica | 0.0025 |
| Anion of Metals | 9.04 |

The first four elements are determined by X-ray fluorescene and the remaining elements are determined by emission spectroscopy. The foregoing more detailed identification of organic components and metals is not one usually made by terephthalic acid manufacturing facilities but is made for research purposes as a starting point, for example, to identify extractable components, or to evaluate the completeness of commercial oxidation of the xylene feed, or to evaluate potential increase of phthalic acids production by some additional oxidation of the phthalic acid precursors present in such residue.

However, the terephthalic acid manufacturing facilities will obtain a partial analysis of the residue to include at least the phthalic acids, toluic acids, benzoic acid and catalyst components to determine on a day-to-day basis the approximate oxidation efficiency, and catalyst metal and solvent discard. Such partial analytical inspections of the residue are as shown in TABLE III to follow.

TABLE III

| PARTIAL ANALYTICAL RESULTS OF RESIDUE FROM TEREPHTHALIC ACID MANUFACTURE | | | | |
|---|---|---|---|---|
| Components | Sample Number | | | |
| In Weight % | 1 | 2 | 3 | 4 |
| Acetic Acid | 0.22 | 3.23 | 3.74 | 3.24 |
| Phthalic Acids | 45.8 | 31.4 | 33.4 | 26.0 |
| Toluic Acids | 5.2 | 12.3 | 12.9 | 22.6 |
| 4-CBA[1] | 1.05 | 4.56 | 4.82 | 9.1 |
| Benzoic Acid | 20.2 | 27.6 | 26.0 | 19.8 |
| Trimellitic Acid | 5.4 | 4.0 | 4.3 | 3.8 |
| OLB Compounds[2] | 0.2 | 4.1 | 4.4 | 0.9 |
| HB Compounds[3] | — | 7.5 | 5.8 | 0.4 |
| Cobalt | 0.69 | 0.49 | 0.5 | 1.35 |
| Manganese | 1.79 | 1.22 | 1.3 | 2.48 |
| Bromine | 2.59 | 1.49 | 1.5 | 2.5 |

[1]"4-CBA" is 4-carboxybenzaldehyde (p-formylbenzoic acid).
[2]"OLB Compounds" are other lower boiling compounds.
[3]"HB Compounds" are higher boiling (higher than trimellitic acid) compounds.

The residue from manufacture of isophthalic acid by air oxidation of m-xylene in an acetic acid reaction medium and in the presence of catalysis provided by cobalt, manganese and bromine is quite similar to the residue from the manufacture of terephthalic acid by the same oxidation of p-xylene. The manufacture of the anhydride (intramolecular) of trimellitic acid (TMA) can produce two residues. One residue is obtained after precipitating and separating impure trimellitic acid from the acetic acid solution of the catalyst (Co—Mn—Br) system and then evaporating the acetic acid. The second residue is obtained after dehydration of impure trimellitic acid (TMLA) to its impure anhydride and evaporating a partially purified anhydride. The compositions of such TMLA and TMA residues and the residue from isophthalic acid (IA) manufacture are characterized in TABLE IV to follow.

TABLE IV

| CHARACTERIZATION OF RESIDUES FROM THE MANUFACTURE OF ISO-PHTHALIC ACID AND TRIMELLITIC ANHYDRIDE | | | |
|---|---|---|---|
| Component, | RESIDUE | | |
| In Weight % | IA | TMLA | TMA |
| Acetic Acids | 0.11 | 1.58 | 0 |
| Phthalic Acids | 39.8 | 12.3 | 1.0 |
| Toluic Acids | 1.8 | 0 | 0 |
| Aldehydes | 0.09 | 0.53 | 1.4 |
| Benzoic Acid | 24.1 | 0.5 | 0 |
| Trimellitic Acid | 2.5 | 38.6 | 65.2[1] |
| OLB Compounds[2] | 1.7 | 4.7 | 1.9 |
| HB Compounds[3] | 5.3 | 0.94 | 0.4 |
| Cobalt | 0.48 | 1.17 | 2.51 |
| Manganese | 1.27 | 0.28 | 0.87 |
| Bromine | 2.6 | 0.94 | 0.15 |

[1]Trimellitic acid anhydride
[2]See TABLE III
[3]See TABLE III

The residues from the manufacture of phthalic anhydride to interest for use in the practice of the present invention are obtained from two different oxidation processes. The residue from the first of such processes is obtained after evaporation of acetic acid and water from the liquid portion of the oxidation effluent from the air oxidation of o-xylene in an acetic acid solution of the Co—Mn—Br catalyst system after precipitating and recovering o-phthalic acid or its anhydride from the oxidation effluent. Such residue contains the components and their concentrations substantially the same as in the residues characterized by TABLES I through III. The residue from the second type of oxidation process is obtained by heating the oxidation effluent to convert o-phthalic acid to its anhydride and evaporate the anhydride and water when such effluent is produced by the air oxidation of liquid o-xylene in liquid o-phthalic acid containing the Co—Mn—Br system of catalysis. Since such oxidation does not use an extraneous solvent, it is hereafter sometimes referred to as the "neat oxidation" process. Such residue from the second type of oxidation process comprises 50 to 85 weight percent phthalic anhydride as a flux for higher boiling materials; e.g., iso- and terephthalic acid, trimellitic acid, metal (Co and Mn) phthalates or acetates, and oxygen-containing both coupled and fused ring compounds: di-, tri- and tetracarboxy-substituted biphenyl and benzophenone and dicarboxyfluorenone. In TABLE V to follow there are given the components and their concentrations in weight percent of such residues from said second type of o-xylene oxidation process.

In TABLE V "PAN" is used to designate phthalic anhydride and "2-CBA" is used to designate 2-carboxybenzaldehyde.

TABLE V
NEAT OXIDATION RESIDUES

| Component, Weight % | Residue Number | | | | |
|---|---|---|---|---|---|
| | 1 | 2 | 3 | 4 | 5 |
| PAN | 72.2 | 77.4 | 65.7 | 84.5 | 57.3 |
| o-Toluic Acid | 0.03 | 0.23 | 0.15 | 0.04 | 0.1 |
| Phthalide | 0.01 | 0.2 | 0.18 | 0.001 | 0.3 |
| 2-CBA | 0.77 | 1.0 | 1.03 | 0.41 | 1.65 |
| Benzoic Acid | 0.56 | 1.03 | 0.69 | 0.60 | 1.8 |
| Other Aromatics | 20.7 | 16.0 | 26.8 | 11.5 | 22.7 |
| Cobalt | 1.14 | 1.08 | 1.36 | 0.62 | 0.58 |
| Manganese | 3.38 | 2.29 | 3.34 | 1.85 | 1.13 |
| Bromine | 1.32 | 0.90 | 0.78 | 0.87 | 1.01 |

Also useful in the practice of the present inventive hydropyrolysis are the undissolved solids portion of the residues after the extraction of the residues with water to remove catalyst metals for reuse in the oxidation from which the metal-containing residue originated. Such undissolved solids portion is hereafter referred to as "extracted residue". In TABLE VI to follow characteristics of such extracted residues are given.

TABLE VI
EXTRACTED RESIDUES

| Components, Weight % | Of Sample 1 TABLE III | Of Sample 3 TABLE III | Of Neat Oxidn. Residue |
|---|---|---|---|
| Aldehydes | 1.57 | 5.84 | 1.03 |
| Benzoic Acid | 18.1 | 31.4 | 1.7 |
| Toluic Acids | 1.61 | 16.0 | 0 |
| Phthalic Acids | 56.4 | 37.6 | 5.6 |
| OLB Compounds | 0.4 | 0.78 | 41.0 |
| HB Compounds | 8.0 | 3.6 | 0.2 |
| Cobalt | 0.18 | 0.03 | 0.16 |
| Manganese | 0.49 | 0.10 | 0.28 |
| Bromine | 0.51 | 0.09 | 0.35 |

EXAMPLE I

The continuous non-catalytic pyrolysis step is conducted in a 16 mm internal diameter stainless steel tube having a wall thickness of 3 mm, a length of 900 mm of which 380 mm is heated in an electric furance, a conical feed hopper in flow communication with the inlet at one end of the tube, an outlet at the other end of the tube for discharge of char and an internal 12.7 mm diameter stainless steel helical screw driven by a variable speed chain drive. The screw transports the residue from the bottom of the feed hopper through the tube and, as decarboxylation and decarbonylation progress during the non-catalytic pyrolysis, transports the resulting char and any carrier particulates out of the tube to the discharge outlet. Nitrogen gas flow at a rate of 2.9 ml/sec. is provided for flow through the feed hopper and pyrolysis tube. Provisions are made to collect the char, the liquid aromatic hydrocarbon trapped by cooling with a slurry of solid carbon dioxide in isopropanol. ;p The screw drive is adjusted for a 10–15 minute flow of residue through the tube which provides a residence time in the hottest portion of the tube of about 5 minutes. Carbon dioxide is trapped by asbestos-sodium hydroxide absorbent which is assayed gravimetrically. The liquids collected by the $CO_2$-isopropanol traps and the gas passing through the system are analyzed as before described.

During decarboxylation and decarbonylation the residue melts and while such thermal decomposition is occurring a porous char forms which tends to stick to the walls of the tube and the hot surfaces of the screw conveyor. To prevent plugging of the tube an inert and thermally stable particulate solid, silica sand, is used as solid carriers for the porous char. The amount of char formed can then be determined gravimetrically from the before and after use weights of the carrier. The silica sand carrier used has a particle size of from 0.589 to 0.833 mm diameter. The residue from terephthalic acid manufacture is comminuted to smaller than 0.833 mm diameter but larger than 0.701 mm diameter (i.e., to pass through U.S. Sieve of 20 mesh but collect on U.S. Sieve of 25 mesh), mixed with the sand in the weight ratio of sand to residue of 6:1.

TABLE VII

| | |
|---|---|
| Pyrolysis, °C. | 750 |
| Residue Charge, gm | 100 |
| $N_2$ Flow, ml/sec. | 2.9 |
| Char, gm | 7.7 |
| Wt.% Residue | 7.7 |
| $CO_2$, gm | 34.2 |
| $CO_2$ wt.% Residue | 34.2 |
| Other Gases, wt.% Residue | |
| Benzene | 18.4 |
| Toluene | 3.6 |
| Other Aromatics | 3.6 |
| Gas Product to $Ca(OH)_2$ wt. ratio | 0.2:1.0 |
| Br Content before $Ca(OH)_2$ treatment, wt.% | 0.84 |
| Br Content After $Ca(OH)_2$ treatment, wt.% | 0.17 |
| Incineration of Gas Product from 1.0 kg TAR, K cal. | 2500 |

The char product yield from the above incineration will, per 1.0 kg TAR fed to pyrolysis, provide an additional 430 K cal. for unextracted char and 600 K cal. for acetic acid extracted char.

EXAMPLE 2

The conduct of the continuous non-catalytic pyrolysis step of this illustrative example of the present invention is in a fluidized bed of 3558 grams of silica and particles having a size of from 0.210 up to 0.297 mm diameter. Said bed of silica sand is contained in a vertical stainless steel (316 S.S.) pipe of 101.6 mm internal diameter, 3 mm wall thickness and 1220 mm length. The sand is contained in the lower 305 mm length of the pipe. The pipe is heated by variable energy input external electric resistance heaters fastened to the outer wall of the pipe. The lower end of the pipe is fastened to an inverted cone of 316 S.S. stainless steel. The apex of the conical bottom of the apparatus is fitted with an inlet for charging a gas to fluidize the silica bed. The cone also has a slurry feed inlet near the junction of the inverted cone and the pipe to which there can be directly attached either a feed tube or a modified feed tube extending into and through said feed inlet upwardly into the bed and terminating about 100 mm above the junction of the cone and pipe. The feed tube connected directly to the slurry feed inlet to the cone is used when the carrier gas is nitrogen. The feed tube which extends into the bed is used when air and nitrogen or oxygen and nitrogen comprise the fluidizing gas to decrease the chance of combustion of the aromatic (benzene and toluene) hydrocarbon products. Both slurry feed tubes at a point prior to their attachment to or entry in the feed inlet have connections for a valved steam line so that steam can be injected with the feed slurry to maintain its temperature and that of the feed tube at or slightly above 80° C.

The upper 915 mm of the vertical pipe functions as a gas-solids disengager zone. The top of the pipe is attached to a vapor-gas transfer line which is tapped for a sampling line of 316 S.S. type stainless steel tubing having a 4.93 mm internal diameter and a 0.71 mm wall thickness. Said sampling line is attached to the inlet of a vertical down-flow water-cooled condenser about 1830 mm long fitted to a condensate receiver which in turn is attached to a particulate trap and then to a vacuum pump which discharges through a wet test meter of from 0 up to 453 standard liters per hour wet gas flow. The wet test meter in turn discharges into an on-line gas chromatograph unit having both flame ionization and thermal conductivity detectors. Nitrogen is used as the internal standard in said unit. Such gas chromatograph unit has the capability of performing a complete gas analysis for $H_2$, $N_2$, CO, $CO_2$, $CH_4$, $C_6H_6$ and $C_7H_8$ from one sample.

The operating conditions and results therefrom are hereafter reported in TABLES IX and X wherein "TAR" is residue from terephthalic acid residue.

TABLE IX

NON-CATALYTIC PYROLYSIS OF TAR SUSPENDED IN WATER IN BED OF SILICA PARTICLES FLUIDIZED WITH NITROGEN GAS

| Example No. | 2 | 3 | 4 | 5 |
|---|---|---|---|---|
| Suspension: | | | | |
| Water, wt. % | 30 | 30 | 30 | 30 |
| TAR, wt. % | 70 | 70 | 70 | 70 |
| Operating Conditions: | | | | |
| Temperature, °C. | 710 | 755 | 740 | 740 |
| TAR, gms/hr. | 1220 | 1800 | 1600 | 1100 |
| $N_2$, gms/hr. | 730 | 730 | 730 | 730 |
| Gas Product Component Yield: | | | | |
| $H_2$, wt. % | 3.2 | 4.1 | 1.6 | 4.9 |
| CO, wt. % | 10.4 | 26 | 9.7 | 32 |
| $CO_2$, wt. % | 60 | 34 | 73 | 80 |
| $CH_4$, wt. % | 4.4 | 2.3 | 0.7 | 0.5 |
| $C_6H_6$, wt. % | 28 | 34 | 42 | 35 |
| $C_7H_8$, wt. % | 1.7 | 4.5 | 2.5 | 2.8 |
| Gas Product to limestone wt. ratio | 0.2: | 0.2: | 0.2: | 0.2: |
| | 1.0 | 1.0 | 1.0* | 1.0* |
| Before treatment | | | | |
| Br, wt. % | 0.47 | 0.30 | 0.38 | 0.32 |
| After treatment | | | | |
| Br, wt. % | 0.094 | 0.060 | 0.076 | 0.064 |
| Incineration of Gas Product From | | | | |

TABLE IX-continued

NON-CATALYTIC PYROLYSIS OF TAR SUSPENDED IN WATER IN BED OF SILICA PARTICLES FLUIDIZED WITH NITROGEN GAS

| Example No. | 2 | 3 | 4 | 5 |
|---|---|---|---|---|
| 1.0 kg TAR, K cal | 4600 | 5800 | 5100 | 5900 |

*The limestone is dolomite.

The char yield from the above fluidized bed non-catalytic pyrolysis is quite low; e.g., 1.0 wt.%, to be considered for combustion except upon recycle of the sand to heat the sand particles.

TABLE X

NON-CATALYTIC PYROLYSIS OF TAR SUSPENDED IN WATER IN BED OF SILICA PARTICLES FLUIDIZED WITH NITROGEN AND AIR

| Example No. | 6 | 7 |
|---|---|---|
| Suspension: | | |
| Water, wt. % | 30 | 30 |
| TAR, wt. % | 70 | 70 |
| Operating Conditions: | | |
| Temperature, °C. | 770 | 770 |
| TAR, gms/hr. | 1100 | 1100 |
| $N_2$, gms/hr. | 590 | 590 |
| $O_2$, gms/hr. | 180 | 180 |
| Gas Product Component Yield: | | |
| $H_2$, wt. % | 0.073 | 0.16 |
| CO, wt. % | 4.3 | 3.83 |
| $CO_2$, wt. % | 60 | 58.1 |
| $CH_4$, wt. % | 0.34 | 0.14 |
| $C_6H_6$, wt. % | 30 | 28 |
| $C_7H_8$, wt. % | 1.9 | 1.2 |
| Br Content of Gas Product, wt. % | 0.52 | 0.54 |
| Gas Product to $CaCO_3$, wt. ratio | 0.2:1.0 | 0.2:1 |
| wt. % Br after $CaCO_3$ Contact, wt. % | 0.10 | 0.11 |
| Incineration of Gas Product From | | |
| 1.0 kg TAR, K cal. | 3200 | 3000 |

The invention claimed is:

1. A method for prevention of bromine-containing particulates from discharge into the atmosphere upon incineration of a solid residue obtained from the manufacture of a benzene di- or tricarboxylic acid by the oxidation of benzene di- or trimethylbenzene in the liquid phase with air in the presence of catalysis provided by a combination of a source of bromine with one or more of cobalt or manganese metal oxidation catalyst; which method comprises (1) subjecting said solid residue in comminuted form or such form suspended in water admixed with an inert particulate solid whose particles are quiescent or in motion as in a fluid bed, expanded bed or a bed made ebullient by passage of inert gas through the bed, to continuous pyrolysis in zone heated to a temperature of at least 700° C. whereat at least a gaseous product is formed which contains at least hydrogen, oxides of carbon, methane, benzene, and toluene and bromine-containing compounds, (2) contacting said gaseous product with a carbonate, hydroxide or oxide of calcium or mixture of calcium and magnesium and then (3) incinerating the gaseous product or the portion thereof after removal of benzene and toluene.

2. The method of claim 1 wherein the pryolysis temperature is from 700° C. up to 900° C.

3. The method of claim 2 wherein the solid residue is from the manufacture of terephthalic acid, such solid residue is comminuted to a particle size of from 0.21 up to 0.297 mm diameter and suspended in water to provide a suspension containing from 30 up to 50 weight percent water, combining said suspension with a bed of silica sand particles fluidized with nitrogen gas or a mixture of nitrogen gas and air and maintained at a temperature of from 730° C. to 750° C., and the gaseous product is contacted with ground limestone having a particle size of from 1.40 mm up to 2.80 mm diameter before incineration of the gaseous product or its portion after removing benzene and toluene.

* * * * *

UNITED STATES PATENT OFFICE
CERTIFICATE OF CORRECTION

Patent No. 4,255,590      Dated March 10, 1981

Inventor(s) John K. Allen

It is certified that error appears in the above-identified patent and that said Letters Patent are hereby corrected as shown below:

Patent Reads

| Page | Line | | |
|------|------|---|---|
| 1 | 37 | "calcium" and should read | --cadmium-- |
| 1 | 57 | "July 29" and should read | --July 27-- |
| 1 | 68 | "isoand" and should read | --iso- and-- |
| 5 | 58 | "fluorescene" and should read | --fluorescence-- |
| 6 | 63 | "to" and should read | --of-- |
| 8 | 14 | "isopropanol. ;p The" and should read --isopropanol. The-- | |
| 8 | 63 | "and" and should read | --sand-- |
| 10 | 46-47 | "in zone" and should read | --in a zone-- |
| 10 | 54 | "pryolysis" and should read | --pyrolysis-- |

Signed and Sealed this

Eighth Day of September 1981

[SEAL]

Attest:

GERALD J. MOSSINGHOFF

Attesting Officer     Commissioner of Patents and Trademarks